United States Patent [19]

Sakakibara

[11] Patent Number: 5,450,464
[45] Date of Patent: Sep. 12, 1995

[54] X-RAY DIAGNOSTIC APPARATUS CAPABLE OF ALIGNING EXAMINED SPOT IN REAL TIMING WITH FLOW OF IMAGE FORMING AGENT

[75] Inventor: Jun Sakakibara, Tochigiken, Japan

[73] Assignee: Kabushiki Kaisha Toshiba, Kawasaki, Japan

[21] Appl. No.: 194,388

[22] Filed: Feb. 10, 1994

[30] Foreign Application Priority Data

Feb. 17, 1993 [JP] Japan .................................. 5-027067

[51] Int. Cl.$^6$ .............................................. H05G 1/64
[52] U.S. Cl. ..................................... 378/98.2; 378/196
[58] Field of Search ............................ 378/98.2, 196

[56] References Cited

U.S. PATENT DOCUMENTS

| | | | |
|---|---|---|---|
| 4,477,923 | 10/1984 | Baumann et al. | 378/98.12 |
| 4,536,790 | 8/1985 | Kruger et al. | 379/98.2 |
| 5,111,492 | 5/1992 | Klausz | 378/98.2 |

FOREIGN PATENT DOCUMENTS 3-53772  3/1991  Japan .

*Primary Examiner*—Craig E. Church
*Attorney, Agent, or Firm*—Oblon, Spivak, McClelland, Maier, & Neustadt

[57] ABSTRACT

An X-ray diagnostic apparatus capable of automatically and accurately moving the supporting member in strict accordance with flow of an image forming agent injected into a blood vessel of patient. The X-ray diagnosis apparatus includes a bed on which the patient is placed to be examined; an X-ray generating unit for generating and transmitting an X-ray toward the patient; an X-ray image photographing unit, for photographing an X-ray image radiated through the patient; a display monitor for displaying an image photographed by the X-ray photographing unit; a flow-rate measuring system for measuring a flowing rate of the image forming agent according to the X-ray image photographed; and a position-changing device for automatically changing a spot of the patient to be photographed by the photographing unit according to the flowing rate measured by the flow-rate measuring system.

7 Claims, 3 Drawing Sheets

X-RAY DIAGNOSTIC APPARATUS CAPABLE OF ALIGNING EXAMINED SPOT IN REAL TIMING WITH FLOW OF IMAGE FORMING AGENT

BACKGROUND OF THE INVENTION

1. Technical Field

The present invention relates to an X-ray diagnostic apparatus, and it particularly relates to a technique in which a photographing region is moved in response to injection of image forming agent or contrast medium.

2. Background Art

In recent years, there has been rapidly developed an X-ray diagnostic apparatus which combines and consists of an image intensifier that converts an X-ray image to an optical image, and other image processing technology where the optical image is photographed to be converted to a video signal and then the video signal is digital-image-processed so as to be displayed on a display monitor.

When such an X-ray diagnostic apparatus is utilized, an operator such as a doctor or an X-ray technician determines a position thereof, viewing a television monitor that displays a fluoroscopic image, so that a desired photographing can be performed.

However, in X-ray photography in which the image forming agent is injected into blood vessels, it is difficult to position an examined biological body and take a proper timing for photographing the biological body. In order to overcome such a problem, it is required for the operator to have sufficient experience and trained intuition.

Particularly in photography of lower limb using the image forming agent, there are many photographing spots, and flow rates of blood differs at a major portion and a peripheral portion of the biological body. Therefore, in the conventional practice, the operator moves a supporting member (bed portion) to photograph a desired portion of the biological body in a manner that the operator observes the motion of the image forming agent viewing the television monitor and he predicts a next motion of the image forming agent based on the observation.

As mentioned above, a burden is heavy to the operator in a photographing technique where the supporting member is manually moved repeatedly viewing the fluoroscopic image. Moreover, there are caused many unsuccessful photographic results, for example, where the image forming agent is not photographed in the photographing image region. Thus, it is difficult to have desired photographing images in the conventional practice.

SUMMARY OF THE INVENTION

In view of the foregoing drawbacks, it is therefore an object of the present invention to provide an X-ray diagnostic apparatus capable of automatically moving the supporting member in strict accordance with (on real time basis with) flow of the image forming agent.

To achieve the object, there is provided an X-ray diagnosis apparatus comprising: supporting means for placing a biological body thereon to be examined; X-ray generating means for generating an X-ray toward the biological body; X-ray image photographing means, disposed counter to the X-ray generating means, for photographing an X-ray image radiated through the biological body; display means for displaying image photographed by the X-ray photographing means; flow-rate measuring means for measuring a flowing rate of an image forming agent injected into the biological body, in accordance with the X-ray image photographed by the X-ray photographing means; and position-changing means for automatically changing a spot of the biological body to be photographed by the photographing means, in accordance with the flowing rate measured by the flow-rate measuring means.

BRIEF DESCRIPTION OF THE DRAWINGS

These and other objects, features and advantages of the present invention will become more apparent from the following description of the preferred embodiment taken in conjunction with the accompanying drawings, in which.

DETAILED DESCRIPTION OF THE PREFERRED EMBODIMENTS

Features of the present invention will become apparent in the course of the following description of exemplary embodiments which are given for illustration of the invention and are not intended to be limiting thereof. Embodiments of the present invention will now be described with reference to the drawings.

Figure 1:
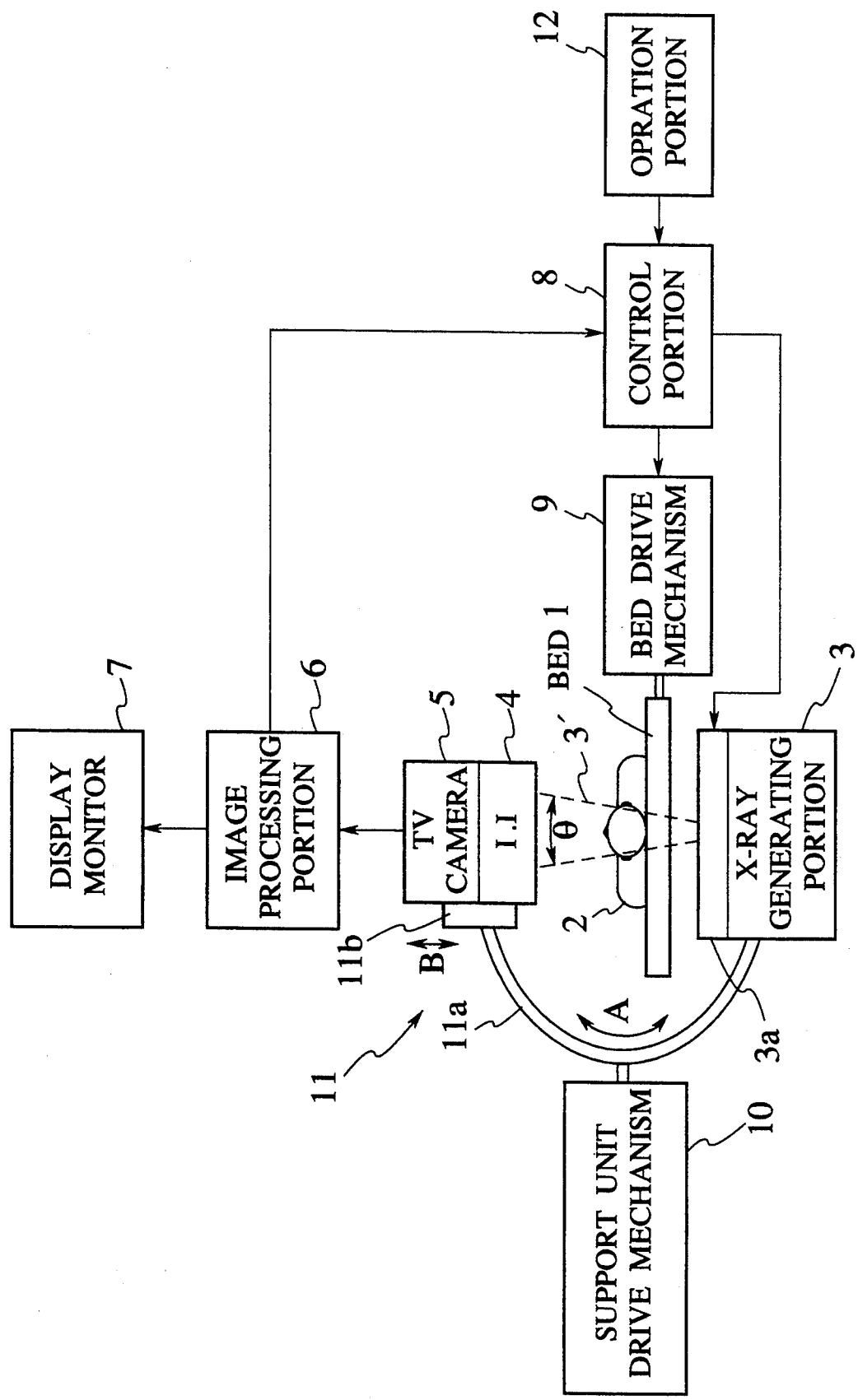
FIG. 1 is a block diagram showing configuration of an X-ray diagnostic apparatus according to the present invention.

FIG. 1 is a block diagram showing configuration of an X-ray diagnostic apparatus according to the present invention.

Referring to FIG. 1, the X-ray diagnostic apparatus comprises:

(1) a bed portion 1 on which a patient 2 lies and which is transferred or moved by a bed drive mechanism 9;

(2) an X-ray generating portion which generates an X-ray and is disposed under the supporting member 1;

(3) an image intensifier (referred to as I.I.) 4 which inputs the X-ray transmitted through the patient 2 and which then converts an inputted X-ray image into an optical image;

(4) a television camera 5 which converts the optical image output from the I.I. 4 into a video signal;

(5) an image processing portion 6 which converts an output signal of the television camera 5 into a digital image data, and which stores the converted data to an image memory;

(6) a display monitor 7 which displays a fluoroscopic image in accordance with a content of the image memory;

(7) a control portion 8 which executes calculation necessary for each part based on the content of the image memory of the image processing portion 6, and which supplies to bed drive mechanism 9 and support unit drive mechanism respective control signals for driving the bed 1 and the supporting unit 11; and (8) an operation portion 12 which inputs an instruction of the operator.

The X-ray generated from the X-ray generating portion 3 is transmitted through the bed 1 and the patient 2 in the form of an X-ray beam 3' having an angle of view $\theta$ and is input to the I.I. 4. The angle of view $\theta$ is controlled by the control portion 8.

The I.I. 4 converts the input X-ray image to an optical image. Output of the I.I. 4 is scanned through an optical system and is converted to the video signal in the television camera 5.

The video signal output from the television camera 5 is A-D converted in the image processing portion 6, and is stored in a video memory (not shown) as intensity data for each pixel.

Figure 3:
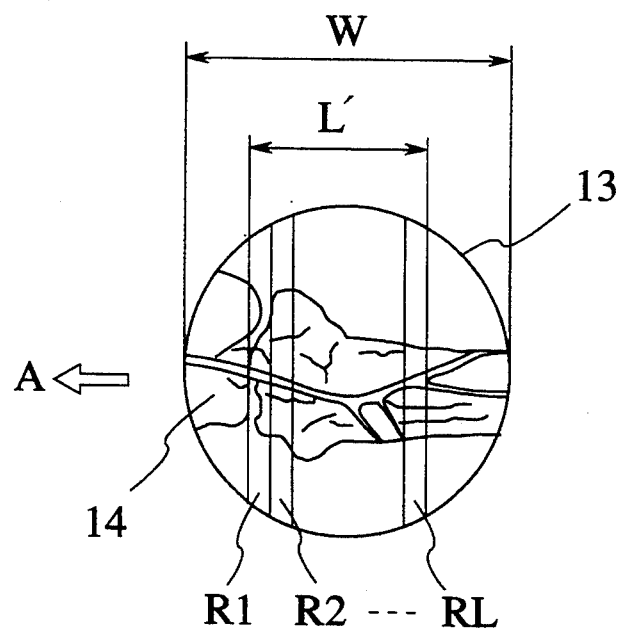
FIG. 3 is an angiographing image where in a central part of the display monitor 13 there are provided infinitely many regions of interest (ROI).

In the display monitor 7, fluoroscopic image is displayed where each pixel is expressed by each density therefor, as shown in FIG. 3.

When taking film-photography, the film is rapidly loaded into a film-photographing system (not shown) in the I.I. 4 automatically or in response to an instruction from the operation portion 12 so that the X-ray beam 3' is image-formed on the film.

The support unit 11 comprises:

(1) a C-shape arm 11a which rotates in the direction indicated with arrow mark A so as to change a radiating angle of the X-ray beam 3' radiated toward the patient 2 and which mechanically connects the X-ray generating portion 3 disposed under the bed 1 and the I.I. 4 disposed above the bed 1;

(2) a slide mechanism 11b which changes a distance between the patient 2 and the I.I. 4 (surface-to-intensifier distance or SID) in a manner that the slide mechanism 11b drives the I.I. 4 and the television camera 5 in the directions of center line indicated with arrow mark B, and which is driven by the support unit drive mechanism 10 in accordance with a control signal from the control portion 8.

A bed drive mechanism 9 moves the bed 1 in horizontal (back-and-forth) directions (i.e., orthogonal directions with respect to drawling sheet of FIG. 1) in accordance with a control signal from the control portion.

An X-ray aperture 3a, the support unit drive mechanism 10 and the bed drive mechanism 9 are controlled by the control portion 8 so that an arbitrary degree of X-ray beam can be shot to an arbitrary part of the patient 2.

Generally speaking, in order to obtain a best-qualified fluoroscopic image or photographing image, a position of an object to be photographed need lie along the central line of the X-ray beam. Thus, when the blood vessels of the patient 2 is injected the image forming agent for the purpose of being photographed, the object to be photographed moves along flowing direction of the image forming agent. Therefore, the bed 1 need be moved along a counter direction to the flow of the image forming agent.

The X-ray diagnostic apparatus according to the present invention is characterized to provide a bed moving system to optlmlze this movement of the bed 1. The control portion 8 serving as a major part for the bed moving system is constructed such that it integrally controls the X-ray aperture 3a, the support unit drive mechanism 10 and the bed drive mechanism 9.

With reference to FIG. 3, there is provided a region of interest having length of L' in the moving direction of bed 1, in a central part of the display monitor picture plane 13.

The region of interest (ROI) is divided into N portions with equally spaced therebetween, in the direction of A. Though N is a definite number (integer), the ROI is preferably divided into infinitely many portions. That there are provided infinitely many portions in ROI means that there are provided as many portions as possible in the ROI. Let us denote respective divided portions R1–RL toward the direction of A.

The control portion 8 is equipped with a mechanism by which an average density of respective portions R1–RL of the ROI is processed. In other words, the control portion 8 has a built-in memory in which density data of the pixel included in each portion of ROI are read out and the density data are averaged for each portion of the ROI so that tile average density is calculated and stored accordingly.

In control portion 8, the average density of each portion of ROI is compared at before and after a predetermined duration so that any change in the average density of each portion of ROI is detected. In the control portion 8, there is provided a system in which a tip of the blood flow is judged to come in when the average density of a certain portion of ROI is increased.

Moreover, the control portion 8 further comprises a time counter which measures time that takes until the blood stream passes the portion of ROI from when the blood stream is judged to be flowed into the portion of ROI in question.

The movement of the bed 1 according to the present invention is controlled in the following manner:

(I) First, at the time of fluoroscopic photography, an average time T is obtained in which the image forming agent 14 crosses N portions of ROI and flows through distance L'. In order to do so, measured by the time counter is time duration from the onset of change in the average density in a certain portion of ROI to a next onset of the change in the average density in an adjacent portion of ROI. Thereby, time which takes for the image forming agent to flow through each portion of ROI is measured, and the average time therefor is obtained. Thereafter, the average time is multiplied by N, so that time T is calculated and the calculated time is stored in the memory.

Figure 4:
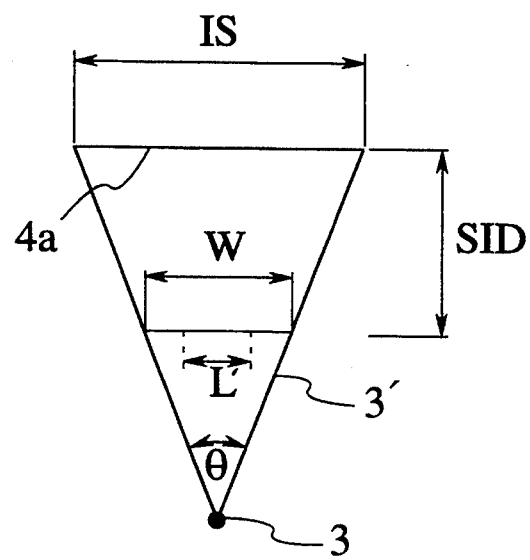
FIG. 4 illustrates relation between the effective length L, dimension IS of X-ray input surface on the I.I. 4, the width W of the display image plane and the distance SID (surface-to-intensifier distance).

(II) Next, with reference to FIG. 4, the control portion 8 measures an effective length L. In other words, the effective length L is obtained from dimension IS of X-ray input surface on the I.I. 4 and a position data on slide mechanism 11b. The distance SID (surface-to-intensifier distance) between the input surface 4a of the I.I. 4 and the examined position of the patient 2 is measured. Thereafter, width W of an image plane is calculated from IS and SID. The effective length L of the examined portion of the patient 2 corresponding to length L' on the image plane is calculated so as to be stored in the memory.

(III) Next, at the time of photographing the part of the biological body to be examined, an instruction signal is fed to the bed drive mechanism 9 from the control portion 8 so that the bed 1 is moved or dislocated by L at time T after the average density of R1 starts to change.

Figure 5:
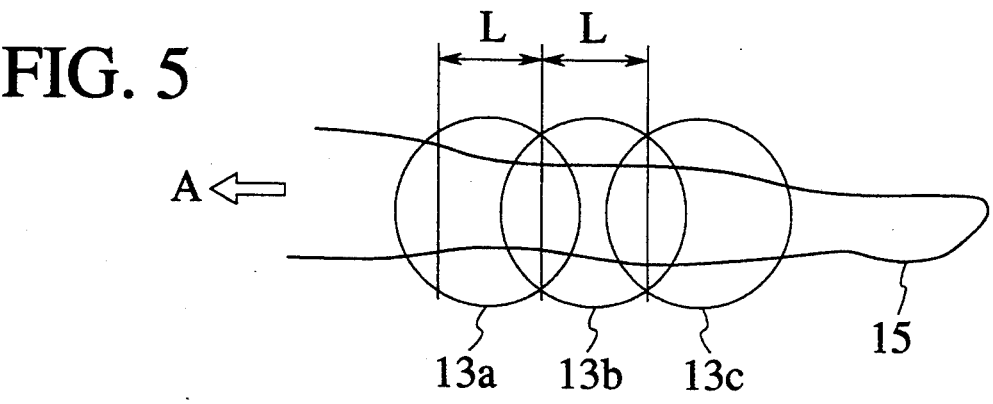
FIG. 5 illustrates that lower limb 15 of the patient 2 lying on the bed 1 is moved in the direction A opposite to that of the flow of the image forming agent, so that the display monitor image plane changes as 13a through 13c.

(IV) The bed drive mechanism 9 activates to move the bed 1 in accordance with the instruction signal sent from the control portion 8. Referring to FIG. 5, the lower limb 15 lying on the bed 1 is moved by distance L, in the direction opposite to that of the image forming agent, for every time T. As a result thereof, every time of photographing instance, the image forming agent is observed, without fall, in the image region L' in the display monitor image plane (13a, 13b, 13c).

It shall be appreciated that in the moving-rate measuring means a preselected value may be regarded as the flowing rate of the agent and is output as such when an actually observed flowing rate does not fall within a predetermined range.

In order to avoid malfunction concerning a timing to detect a blood flow and the movement of the bed or the supporting unit, the region of interest (ROI) on the display is divided into as many as partitions thereof as possible. Thereby, the calculation of the average flow rate of the image forming agent is safely secured so that the timing for movement for the bed or supporting unit can be optimally controlled. At the same time, difference in the major portion and the peripheral portion is preferably adjusted also.

There sometimes occurs a case where it is not possible to calculate the average flow rate under photography or the calculation is carried out mistakingly, so that the timing for movement of the bed or supporting unit becomes erroneous. In such an event where the calculated values are greater than the predetermined upper limit, the moving timing can be controlled in a manner that certain known flow rate is regarded as an initial value. Thereby, the X-ray photography need not be carried out again because of the impossibility of calculation, so that a degree for the patient to be X-ray radiated can be minimized, thus achieving safe X-ray diagnosis.

Figure 2:
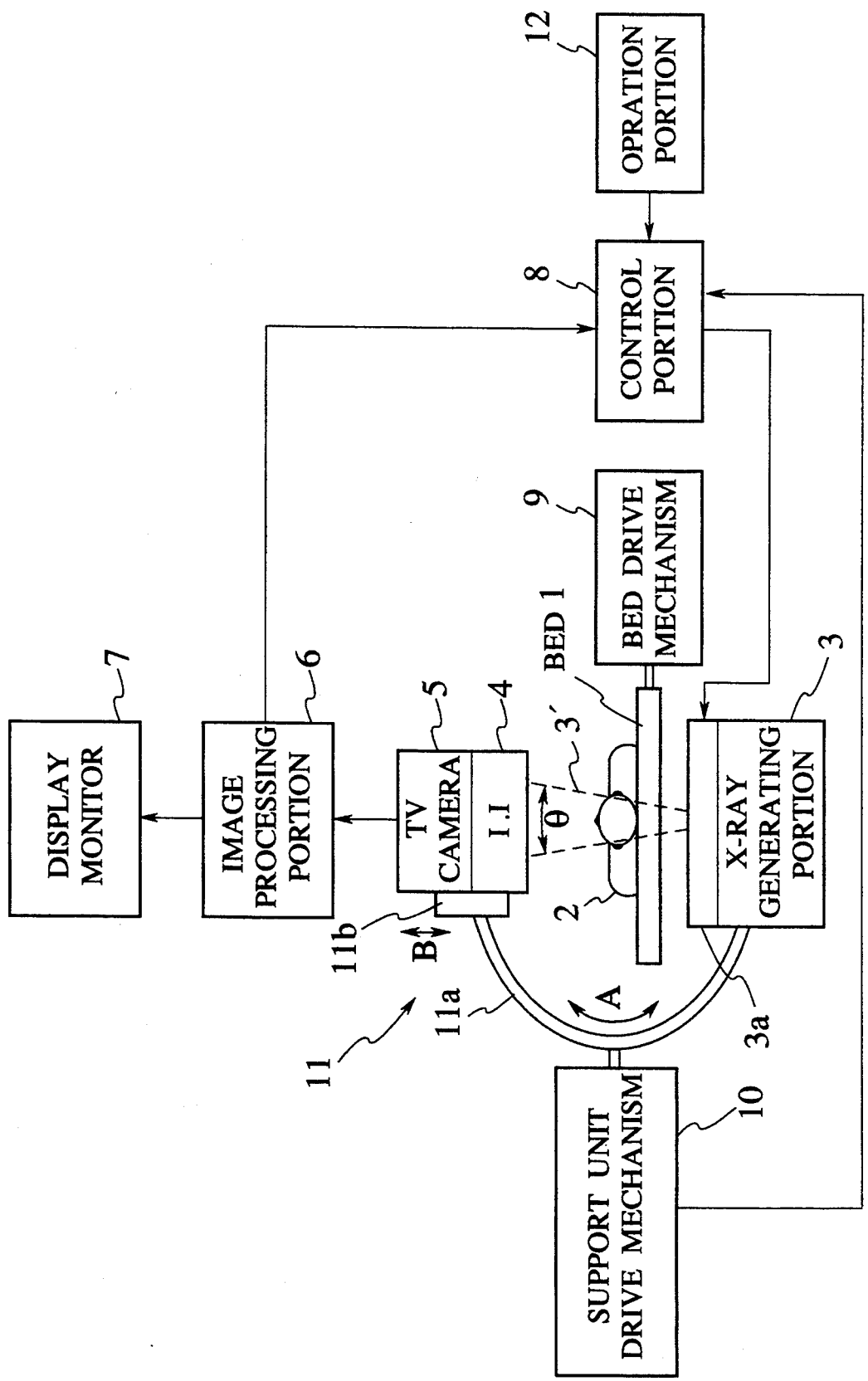
FIG. 2 is a block diagram showing the X-ray diagnostic apparatus according to another embodiment for the present invention.

FIG. 2 shows another embodiment based on the aforementioned basic embodiment. The block diagram shown in FIG. 2 indicates that the support unit 11 plays a role of being moved, while, in contrast, the bed 1 is moved in the basic configuration shown in FIG. 1. In this connection, the control portion 8 is directly connected to the support unit drive mechanism 10 which plays the role of the bed drive mechanism 9.

In this another embodiment shown in FIG. 2, the patient 2 lying on the bed 1 is stationary. Thus, pain that the patient may take is minimized. In this another embodiment, there can be obtained same advantageous aspects as mentioned in the above basic configuration and method.

As have been described, the ROI is divided into as many partitions as possible, and each divided partition serves as a ROI as well. When the average density starts to change, it is then Judged that the image forming agent is flowing. Then, the flow rate of the image forming agent is calculated so that the bed on which the patient lies or the supporting unit is properly aligned for a next step by calculating time for moving the bed or the supporting unit. Since there are provided as many ROIs as possible, the movement of the bed or the supporting unit for the next step can be stopped in the event that the flow of the image forming agent is stopped. Moreover, the novel X-ray diagnostic apparatus of the present invention can be implemented to both DSA (digital subtraction angiography) and DA (digital angiography).

In summary, by employing the X-ray diagnostic apparatus according to the present invention, the patient lying on the bed is moved strictly in accordance with the flow of the image forming agent. Alternately, the support unit can be moved strictly in accordance with the flow of the image forming agent. Thereby, a burden on the operator is significantly reduced in the event of X-ray photographing using the image forming agent injected to the patient. Moreover, time necessary for photographing is reduced so as to smoothly perform the X-ray photography.

Besides those already mentioned above, many modifications and variations of the above embodiments may be made without departing from the novel and advantageous features of the present invention. Accordingly, all such modifications and variations are intended to be included within the scope of the appended claims.

What is claimed is:

1. An X-ray diagnostic apparatus comprising:
   a bed on which a biological body is placed to be examined;
   X-ray generating means for generating and transmitting an X-ray toward the biological body;
   X-ray imaging means, for imaging an X-ray image radiated through the biological body;
   display means for displaying an image obtained from the X-ray imaging means;
   flow-rate measuring means for measuring a flowing rate of an image forming agent injected into the biological body, in accordance with the X-ray image obtained from the X-ray imaging means, the flow-rate measuring means providing a region of interest which is plurally divided into partitions of image planes so that the flow-rate of the image forming agent is calculated based on a change in an average density of the agent in each of said partitions; and
   position changing means for automatically aligning a portion of the biological body to be photographed by the photographing means, in accordance with the flowing rate measured by the flow-rate measuring means.

2. The apparatus of claim 1, wherein in the flow-rate measuring means a preselected value is regarded as the flowing rate of the image forming agent and is output as such when an observed flowing rate does not fall within a predetermined range.

3. The apparatus of claim 1, wherein the flow-rate measuring means includes:
   control means for calculating an average density of respective divided partitions,
   wherein the control means includes memory means for storing calculated density data.

4. The apparatus of claim 1, wherein the flow-rate measuring means includes counter means for measuring time during which a tip of the image forming agent enters into a partition divided in the region of interest and then passes through the partition.

5. The apparatus of claim 1, wherein the position-changing means is provided on the bed so that a position of the biological body lying on the bed is changed.

6. The apparatus of claim 1, wherein the position-changing means is provided such that the X-ray imaging means is moved.

7. A method of examining a biological body by an X-ray diagnostic apparatus where an image forming agent is injected into the biological body, the method comprising the steps of:
   providing N regions of interest in a display monitor image plane, N being an integer greater than 1;
   determining an average time T in which the image forming agent crosses said N regions of interest and flows through a distance l in the display monitor image plane;
   measuring an effective and actual length L from l; and
   automatically moving the biological body by distance L at time T after the average density of a first region of interest starts to change.

* * * * *